United States Patent
Kim et al.

(10) Patent No.: US 11,571,687 B2
(45) Date of Patent: Feb. 7, 2023

(54) METHODS FOR RECOVERING AND REUSING SELECTIVE HOMOGENEOUS HYDROGENATION CATALYST

(71) Applicant: HANWHA SOLUTIONS CORPORATION, Seoul (KR)

(72) Inventors: Youngjin Kim, Daejeon (KR); Namjin Jang, Daejeon (KR); Kyuho Song, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 0 days.

(21) Appl. No.: 17/413,582

(22) PCT Filed: Aug. 27, 2019

(86) PCT No.: PCT/KR2019/010922
§ 371 (c)(1),
(2) Date: Jun. 14, 2021

(87) PCT Pub. No.: WO2020/130280
PCT Pub. Date: Jun. 25, 2020

(65) Prior Publication Data
US 2022/0048017 A1    Feb. 17, 2022

(30) Foreign Application Priority Data
Dec. 19, 2018 (KR) .......... 10-2018-0165267

(51) Int. Cl.
*B01J 31/40* (2006.01)
*B01J 31/24* (2006.01)
(Continued)

(52) U.S. Cl.
CPC ....... *B01J 31/4053* (2013.01); *B01J 31/2409* (2013.01); *C07C 5/05* (2013.01);
(Continued)

(58) Field of Classification Search
CPC .............. B01J 31/4053; B01J 31/2409; B01J 2231/645; B01J 2531/821; C07C 5/05;
(Continued)

(56) References Cited

U.S. PATENT DOCUMENTS 5,128,296 A   7/1992 Matson
5,177,278 A   1/1993 Sanchez
(Continued)

FOREIGN PATENT DOCUMENTS

JP    2002003414 A    1/2002
JP    2004339197 A    12/2004
(Continued)

OTHER PUBLICATIONS

International Search Report dated Dec. 3, 2019.
(Continued)

*Primary Examiner* — Ali Z Fadhel
(74) *Attorney, Agent, or Firm* — Harvest IP Law LLP

(57) ABSTRACT

The present invention pertains to a method for recovering a selective homogeneous hydrogenation catalyst and a method for reusing the recovered selective homogeneous hydrogenation catalyst. The method for recovering a selective homogeneous hydrogenation catalyst comprises: a step for synthesizing cyclododecene by selectively hydrogenating a first reaction solution containing cyclododecatriene, triphenylphosphine, formaldehyde, and ruthenium chloride, wherein a selective homogeneous hydrogenation catalyst is prepared during the selective hydrogenation reaction from the triphenylphosphine, formaldehyde, and ruthenium chloride to synthesize the cyclododecene; and a step for distilling and separating unreacted cyclododecatriene and cyclododecadiene, as well as the product cyclododecene, from a second reaction solution in which the cyclododecene syn-
(Continued)

thesis has been completed, and recovering the selective homogeneous hydrogenation catalyst.

9 Claims, 3 Drawing Sheets

(51) Int. Cl.
 *C07C 5/05* (2006.01)
 *C07C 7/04* (2006.01)
(52) U.S. Cl.
 CPC ............ *C07C 7/04* (2013.01); *B01J 2231/645* (2013.01); *B01J 2531/821* (2013.01)
(58) Field of Classification Search
 CPC ... C07C 7/04; C07C 2527/13; C07C 2601/20; C07C 7/20; C07C 13/275; Y02P 20/52; Y02P 20/584
 See application file for complete search history.

(56) References Cited

U.S. PATENT DOCUMENTS

| | | | |
|---|---|---|---|
| 2008/0275276 A1* | 11/2008 | Teles | ...................... C07C 45/28 568/363 |
| 2018/0346398 A1 | 12/2018 | Liao | |

FOREIGN PATENT DOCUMENTS

| | | |
|---|---|---|
| JP | 2007506694 A | 3/2007 |
| JP | 5331076 B2 | 10/2013 |
| WO | 2005030689 A2 | 4/2005 |

OTHER PUBLICATIONS

European Search Report dated Aug. 29, 2022.
KR Office Action dated Apr. 7, 2022.
JP Notice of Allowance dated Jun. 1, 2022.

* cited by examiner

METHODS FOR RECOVERING AND REUSING SELECTIVE HOMOGENEOUS HYDROGENATION CATALYST

CROSS-REFERENCE TO RELATED APPLICATIONS

This application is a National Stage of International Application No. PCT/KR2019/010922 filed Aug. 27, 2019, claiming priority based on Korean Patent Application No. 10-2018-0165267 filed Dec. 19, 2018.

TECHNICAL FIELD

The present invention relates to methods for recovering and reusing a selective homogeneous hydrogenation catalyst.

BACKGROUND ART

Synthesis of cyclododecene (CDEN) by selective hydrogenation starting from cyclododecatriene (CDT) has frequently been described in literatures, and many studies have been conducted to increase a yield of cyclododecene.

In order for the selective hydrogenation to proceed, a metal ligand catalyst known as Wilkinson's catalyst, that is, a catalyst in which a ligand such as triphenylphosphine (TPP) or CO and a halogen atom bind to a metal such as rubidium (Ru), rhodium (Rh), cobalt (Co), or nickel (Ni) has been used.

In general, a catalyst is a substance that accelerates activation of the whole reaction in a certain reaction system without reacting itself, and is an indispensable substance in the chemical industry. The catalyst is usually present in a small amount in a reaction system and plays its role. In accordance with development of the chemical industry, a use amount of catalysts has increased, and the amount of waste catalysts generated has also rapidly increased. In Korea, which does not have natural resources and relies entirely on imports for industrial raw materials related to precious metals, it is urgently needed to carry out recycling for reusing the precious metals as industrial raw materials by recovering the precious metals from the waste catalysts.

A method for recovering a catalyst after selective hydrogenation performed depending on a state and conditions of the catalyst has been known.

For example, U.S. Pat. No. 4,413,118 discloses a technology for separating a catalyst in which triphenylphosphine and a halogen atom as ligands bind to Group VIII metal by interacting the catalyst with a substance containing a C=S bond. However, there are disadvantages in that a significant time is required for the interaction process and cooling is required to around 0° C.

U.S. Pat. No. 3,715,405 discloses the fact that when a $[Co(CO)_3P(n-C_4H_9)_3]_2$ catalyst is used in selective hydrogenation for producing cyclododecene from cyclododecatriene, the catalyst may be recovered through a phase separation after the reaction without an additional separation technology. However, there are disadvantages in that the amount of catalyst required is large and a solvent is required for the phase separation.

Therefore, methods for recovering and reusing a selective hydrogenation catalyst capable of separating and recovering a selective hydrogenation catalyst by a relatively simple method within a short process time while maintaining both a conversion ratio of cyclododecatriene and a selectivity of cyclododecene at high levels when reusing the recovered selective hydrogenation catalyst, are required.

DISCLOSURE

Technical Problem

In order to solve the above problems, an object of the present invention is to provide methods for recovering and reusing a selective homogeneous hydrogenation catalyst capable of separating and recovering a selective homogeneous hydrogenation catalyst by a relatively simple method within a short process time while maintaining both a conversion ratio of cyclododecatriene and a selectivity of cyclododecene at high levels when reusing the recovered selective homogeneous hydrogenation catalyst.

Technical Solution

In one general aspect, a method for recovering a selective homogeneous hydrogenation catalyst includes: a step of synthesizing cyclododecene by selectively hydrogenating a first reaction solution containing cyclododecatriene, triphenylphosphine, formaldehyde, and ruthenium chloride, the cyclododecene being synthesized by preparation of a selective homogeneous hydrogenation catalyst from the triphenylphosphine, the formaldehyde, and the ruthenium chloride during the selective hydrogenation; and a step of distilling and separating unreacted cyclododecatriene and cyclododecadiene, and the cyclododecene that is a product from a second reaction solution in which the cyclododecene synthesis is completed, and recovering the selective homogeneous hydrogenation catalyst.

The distillation and separation may be performed at a temperature of 100 to 200° C. and a pressure of 0.5 bar or less. The recovering of the selective homogeneous hydrogenation catalyst may be performed at a temperature of 10 to 30° C., and at a pressure of 0.1 bar or less or in a nitrogen atmosphere.

The recovered selective homogeneous hydrogenation catalyst may satisfy the following Relational Expression 1. In the following Relational Expression 1, $C_1$ is a conversion ratio (%) in the initial selective hydrogenation performed before the recovering of the selective homogeneous hydrogenation catalyst, and $C_2$ is a conversion ratio (%) in the selective hydrogenation performed using the recovered selective homogeneous hydrogenation catalyst as a catalyst.

$$90 \leq C_2/C_1 \times 100 \leq 100 \qquad \text{[Relational Expression 1]}$$

The recovered selective homogeneous hydrogenation catalyst may satisfy the following Relational Expression 2. In the following Relational Expression 2, $S_1$ is a selectivity (%) in the initial selective hydrogenation performed before the recovering of the selective homogeneous hydrogenation catalyst, and $S_2$ is a selectivity (%) in the selective hydrogenation performed using the recovered selective homogeneous hydrogenation catalyst as a catalyst.

$$90 \leq S_2/S_1 \times 100 \leq 100 \qquad \text{[Relational Expression 2]}$$

A molar ratio between the ruthenium chloride, the triphenylphosphine, and the formaldehyde may be 1:100 to 300:150 to 500.

The selective hydrogenation may be performed in a stirred-tank reactor provided with a gas induction hollow stirrer. Hydrogen gas present in a gas phase at an upper portion of the stirred-tank reactor may be supplied to the reaction solution through a hollow portion of the gas induction hollow stirrer.

The first reaction solution may further contain a catalyst activator containing acetic acid. The catalyst activator may be added in an amount of 0.01 to 2 parts by weight with respect to 100 parts by mass of the cyclododecatriene.

The selective hydrogenation may be performed at a temperature of 120 to 200° C. and a pressure of 10 to 80 bar.

In another general aspect, a method for reusing a recovered selective homogeneous hydrogenation catalyst includes: a step of synthesizing cyclododecene by selectively hydrogenating a first reaction solution containing cyclododecatriene, triphenylphosphine, formaldehyde, and ruthenium chloride, the cyclododecene being synthesized by preparation of a selective homogeneous hydrogenation catalyst from the triphenylphosphine, the formaldehyde, and the ruthenium chloride during the selective hydrogenation; a step of distilling and separating unreacted cyclododecatriene and cyclododecadiene, and the cyclododecene that is a product from a second reaction solution in which the cyclododecene synthesis is completed, and recovering the selective homogeneous hydrogenation catalyst; and a step of synthesizing cyclododecene by re-adding the recovered selective homogeneous hydrogenation catalyst to a third reaction solution containing cyclododecatriene and secondarily selectively hydrogenating the recovered selective homogeneous hydrogenation catalyst.

Advantageous Effects

In the methods for recovering and reusing the selective homogeneous hydrogenation catalyst according to the present invention, the unreacted cyclododecatriene and cyclododecadiene, the cyclododecene that is the product, the selective homogeneous hydrogenation catalyst, and excessive triphenylphosphine may be separated by only the distillation (evaporation) and separation method, and the selective homogeneous hydrogenation catalyst and the excessive triphenylphosphine that are separated and recovered without an additional subsequent treatment may be used in the next selective hydrogenation as they are.

In addition, in a case where the recovered selective homogeneous hydrogenation catalyst is used, an induction period may be shortened as compared to a case where selective hydrogenation is induced by formation of a selective homogeneous hydrogenation catalyst using a catalyst containing triphenylphosphine, formaldehyde, and ruthenium chloride during the initial reaction. Therefore, productivity may be further increased.

In addition, when the recovered selective homogeneous hydrogenation catalyst is reused, both a conversion ratio of cyclododecatriene and a selectivity of cyclododecene may be maintained at high levels.

Further, since reuse is not necessary even without recovering formaldehyde, harmful effects to the environment and human body may be lowered, which is preferable.

Although the effects are not explicitly mentioned in the present invention, the effects described in the specification anticipated by the technical features of the present invention and the inherent effects thereof are treated as described in the specification of the present invention.

BEST MODE

Figure 1:
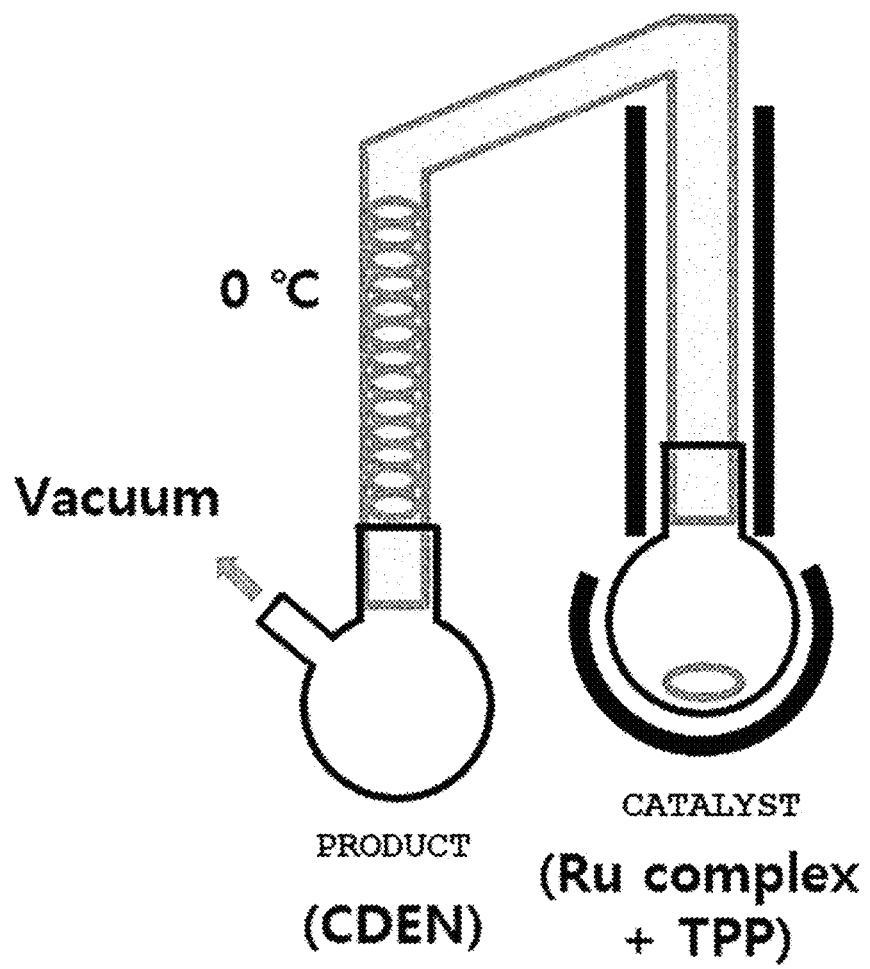
FIG. 1 is a view illustrating a method for recovering a selective homogeneous hydrogenation catalyst according to an embodiment of the present invention.
Figure 2:
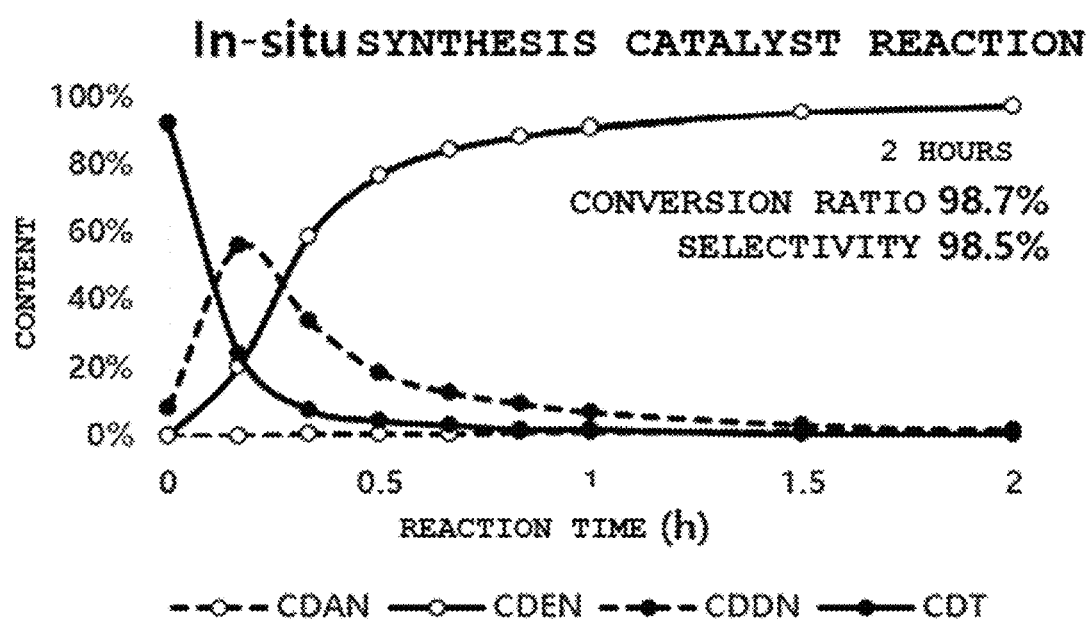
FIG. 2 is a view illustrating a conversion ratio and a selectivity in an initial reaction performed in Example 1.
Figure 3:
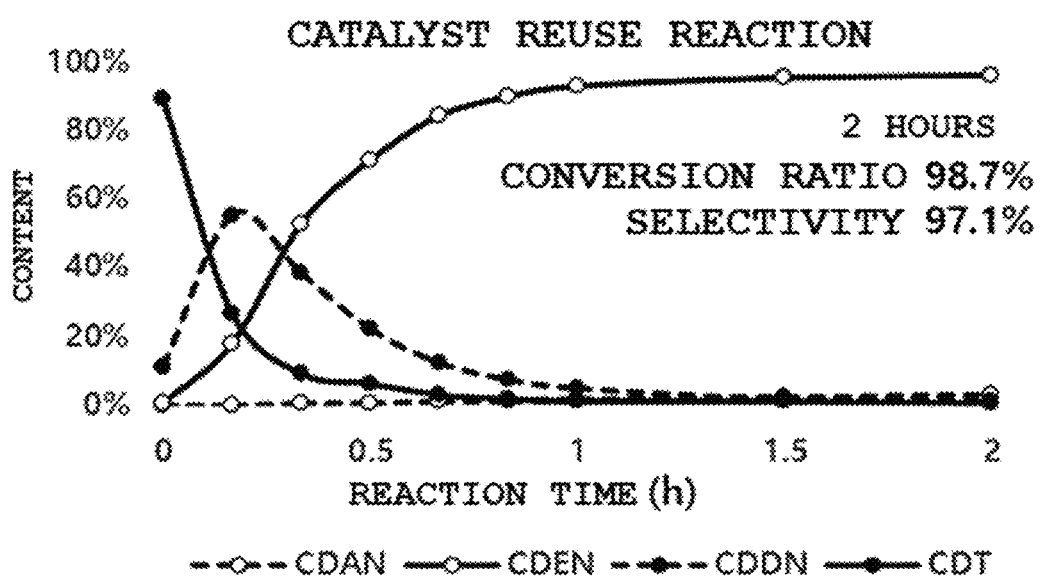
FIG. 3 is a view illustrating a conversion ratio and a selectivity in a second reaction performed using a recovered selective homogeneous hydrogenation catalyst in Example 2.

Hereinafter, methods for recovering and reusing a selective homogeneous hydrogenation catalyst according to the present invention will be described in detail. However, unless otherwise defined, all the technical terms and scientific terms used herein have the same meanings as commonly understood by those skilled in the art to which the present invention pertains, and a description for the known function and configuration unnecessarily obscuring the gist of the present invention will be omitted in the following description.

In addition, in the present specification, the terms "first", "second", "A", "B", "(a)", "(b)", and the like may be used in describing components according to the present invention. These terms are used only in order to distinguish any component from other components, and features, sequences, or the like, of corresponding components are not limited by these terms.

In addition, unless the context clearly indicates otherwise, the singular forms of the terms used in the present specification may be interpreted as including the plural forms.

Unless otherwise defined, a unit of "%" used in the present specification unless specifically mentioned refers to "wt %".

As precious metals, which are rare and expensive due to their low production, are used as a catalyst used in selective hydrogenation for producing cyclododecene from cyclododecatriene, in Korea, which does not have natural resources and relies entirely on imports for industrial raw materials related to precious metals, it is urgently needed to carry out recycling for reusing the precious metals as industrial raw materials by recovering the precious metals from waste catalysts.

The present applicant intends to provide methods for recovering and reusing a selective homogeneous hydrogenation catalyst capable of separating and recovering a selective homogeneous hydrogenation catalyst by a relatively simple method within a short process time while maintaining both a conversion ratio of cyclododecatriene and a selectivity of cyclododecene at high levels when reusing the recovered selective homogeneous hydrogenation catalyst.

Specifically, the method for recovering a selective homogeneous hydrogenation catalyst according to the present invention may include: a step of synthesizing cyclododecene (CDEN) by selectively hydrogenating a first reaction solution containing cyclododecatriene (CDT), triphenylphosphine (TPP), formaldehyde, and ruthenium chloride ($RhCl_3$), the cyclododecene being synthesized by preparation of a selective homogeneous hydrogenation catalyst from the triphenylphosphine, the formaldehyde, and the ruthenium chloride during the selective hydrogenation; and a step of distilling (evaporating) and separating unreacted cyclododecatriene and cyclododecadiene, and the cyclododecene that is a product from a second reaction solution in which the cyclododecene synthesis is completed, and recovering the selective homogeneous hydrogenation catalyst.

As such, the unreacted cyclododecatriene and cyclododecadiene, the cyclododecene that is the product, the selective homogeneous hydrogenation catalyst, and excessive triphenylphosphine may be separated by only the distillation (evaporation) and separation method, and the selective homogeneous hydrogenation catalyst and the excessive triphenylphosphine that are separated and recovered without an additional subsequent treatment may be used in the next selective hydrogenation as they are.

In addition, in a case where the recovered selective homogeneous hydrogenation catalyst is used, an induction period may be shortened as compared to a case where selective hydrogenation is induced by formation of a selective homogeneous hydrogenation catalyst using a catalyst containing triphenylphosphine, formaldehyde, and ruthenium chloride during the initial reaction. Therefore, productivity may be further increased.

In addition, when the recovered selective homogeneous hydrogenation catalyst is reused, both a conversion ratio of cyclododecatriene and a selectivity of cyclododecene may be maintained at high levels.

In addition, since reuse is not necessary even without recovering formaldehyde, harmful effects to the environment and human body may be lowered, which is preferable.

Hereinafter, the methods for recovering a selective homogeneous hydrogenation catalyst according to the present invention will be described in detail.

First, the step of synthesizing the cyclododecene by selectively hydrogenating the first reaction solution containing cyclododecatriene, triphenylphosphine, formaldehyde, and ruthenium chloride, the cyclododecene being synthesized by preparation of the selective homogeneous hydrogenation catalyst from the triphenylphosphine, the formaldehyde, and the ruthenium chloride during the selective hydrogenation may be performed. In this case, for the selective hydrogenation, hydrogen gas ($H_2$) is also added by a general method.

The present step is a step of synthesizing cyclododecene. Cyclododecene may be synthesized by a method to be described below or an existing known method.

Specifically, in the step of synthesizing the cyclododecene, the selective hydrogenation may be performed in a stirred-tank reactor provided with a gas induction hollow stirrer. As such, in a case where the reaction is performed by adopting a method using the gas induction hollow stirrer, reactivity may be secured without an organic solvent commonly used to increase reactivity, and a reaction time may also be significantly reduced.

More specifically, in the step of synthesizing the cyclododecene, the reaction may be performed by rotation and stirring of the gas induction hollow stirrer, and hydrogen gas present in a gas phase at an upper portion of the stirred-tank reactor may be supplied to the reaction solution through a hollow portion of the gas induction hollow stirrer, thereby supplying hydrogen to cyclododecariene. A hollow path is formed inside the gas induction hollow stirrer. Hydrogen gas is introduced through the hollow path and comes into contact with cyclododecatriene, such that the selective hydrogenation may proceed.

Alternatively, cyclododecene may be synthesized by an existing known method.

As a specific example, the cyclododecene may be synthesized by hydrogenation to cyclododecatriene in a solvent containing ethanol, and may be synthesized by a reaction under a catalyst containing triphenylphosphine, formaldehyde, and ruthenium chloride.

Since the ethanol has a high dielectric constant, the reaction between the reactants may be further activated in the selective hydrogenation, such that the conversion ratio and the selectivity may be improved. A use amount of the ethanol is not particularly limited as long as selective hydrogenation to cyclododecatriene may be performed.

Preferably, the amount of ethanol to be added may be 1 to 20 parts by weight, more preferably 2 to 15 parts by weight, and still more preferably 3 to 10 parts by weight, with respect to 100 parts by weight of the cyclododecatriene. However, this is only a preferred example, and the present invention is not limited thereto.

Meanwhile, cyclododecene may be synthesized by preparation of the selective homogeneous hydrogenation catalyst from the triphenylphosphine, the formaldehyde, and the ruthenium chloride during the selective hydrogenation. A homogeneous composite catalyst that is the selective homogeneous hydrogenation catalyst may be $Ru(PPh_3)_2(CO)_2Cl_2$.

Specifically, the triphenylphosphine and the formaldehyde form a complex in the ruthenium chloride and serve as catalysts for the selective hydrogenation.

As a preferred example, a molar ratio between the ruthenium chloride, the triphenylphosphine, and the formaldehyde may be 1:100 to 300:150 to 500. More preferably, the molar ratio between the ruthenium chloride, the triphenylphosphine, and the formaldehyde may be 1:130 to 250:200 to 400. Still more preferably, the molar ratio between the ruthenium chloride, the triphenylphosphine, and the formaldehyde may be 1:170 to 230:250 to 350. Within the above range, the conversion ratio and the selectivity may be significantly improved. However, this is only a preferred example, and the present invention is not limited thereto.

In addition, in an embodiment of the present invention, the first reaction solution may further contain a catalyst activator containing acetic acid. When the acetic acid is added, a reaction of a ruthenium chloride-triphenylphosphine complex catalyst is further activated to further improve the conversion ratio and the selectivity. As a preferred example, the acetic acid may be added in an amount of 0.01 to 2 parts by weight with respect to 100 parts by weight of the cyclododecatriene. More preferably, the acetic acid may be added in an amount of 0.05 to 1.5 parts by weight with respect to 100 parts by weight of the cyclododecatriene. Still more preferably, the acetic acid may be added in an amount of 0.1 to 1 part by weight with respect to 100 parts by weight of the cyclododecatriene. However, this is only a preferred example, and the present invention is not limited thereto.

In an embodiment of the present invention, a use amount of the catalyst containing triphenylphosphine, formaldehyde, and ruthenium chloride is not particularly limited as long as the reaction of the reactants may be sufficiently performed. Preferably, the catalyst containing triphenylphosphine, formaldehyde, and ruthenium chloride may be added in an amount of 1 to 20 parts by weight with respect to 100 parts by weight of the cyclododecatriene. The catalyst containing triphenylphosphine, formaldehyde, and ruthenium chloride may be added in an amount of preferably 1 to 10, and more preferably 1 to 7 parts by weight, with respect to 100 parts by weight of the cyclododecatriene. However, this is only a preferred example to improve the conversion ratio and the selectivity, and the present invention is not limited thereto.

In an embodiment of the present invention, the selective hydrogenation may be performed at a temperature of 120 to 200° C. and a pressure of 10 to 80 bar, more preferably at a temperature of 140 to 180° C. and a pressure of 20 to 60 bar, and still more preferably at a temperature of 150 to 175° C. and a pressure of 20 to 40 bar. However, this is only a preferred example to improve the conversion ratio and the selectivity, and the present invention is not limited thereto.

Next, the step of distilling and separating the unreacted cyclododecatriene and cyclododecadiene, and the cyclododecene that is the product from the second reaction solution in which the cyclododecene synthesis is completed, and recovering the selective homogeneous hydrogenation catalyst may be performed.

As described above, the unreacted cyclododecatriene and cyclododecadiene, the cyclododecene that is the product, the selective homogeneous hydrogenation catalyst, and excessive triphenylphosphine may be separated by only the distillation and separation method, and the selective homogeneous hydrogenation catalyst and the excessive triphenylphosphine that are separated and recovered without an additional subsequent treatment may be used in the next selective hydrogenation as they are.

In an embodiment of the present invention, the distillation and separation may be performed at a temperature of 100 to 200° C. and a pressure of 0.5 bar or less, more preferably at a temperature of 100 to 180° C. and a pressure of 0.3 bar or less, and still more preferably at a temperature of 100 to 150° C. and a pressure of 0.1 bar or less. Within the above range, the unreacted cyclododecatriene and cyclododecadiene, and the cyclododecene that is the product may be effectively distilled and separated.

In an embodiment of the present invention, the recovering of the selective homogeneous hydrogenation catalyst may be performed at a temperature of 10 to 30° C., and at a pressure of 0.1 bar or less or in a nitrogen atmosphere. That is, the temperature raised by the distillation and separation process may be cooled to a room temperature level to recover the selective homogeneous hydrogenation catalyst.

As such, when the recovered selective homogeneous hydrogenation catalyst is reused, both the conversion ratio of the cyclododecatriene and the selectivity of the cyclododecene may be maintained at high levels.

Specifically, the recovered selective homogeneous hydrogenation catalyst may satisfy the following Relational Expression 1.

$$90 \leq C_2/C_1 \times 100 \leq 100 \quad \text{[Relational Expression 1]}$$

In Relational Expression 1, $C_1$ is a conversion ratio (%) in the initial selective hydrogenation performed before the recovering of the selective homogeneous hydrogenation catalyst, and $C_2$ is a conversion ratio (%) in the selective hydrogenation performed using the recovered selective homogeneous hydrogenation catalyst as a catalyst.

More preferably, the recovered selective homogeneous hydrogenation catalyst may satisfy $95 \leq C_2/C_1 \times 100 \leq 100$. Still more preferably, the recovered selective homogeneous hydrogenation catalyst may satisfy $98 \leq C_2/C_1 \times 100 \leq 100$.

In this case, the conversion ratio may be calculated after the selective hydrogenation is performed in a state where reaction conditions such as a content of each of components, a reaction temperature, pressure, and time, and the like are adjusted to be the same as each other. The conversion ratio may be calculated by the following Calculation Formula 1.

$$\text{Conversion ratio (\%)} = (CDT_0 - CDT_1 - CDDN_1)/CDT_0 \times 100 \quad \text{[Calculation Formula 1]}$$

In Calculation Formula 1, $CDT_0$ is the number of moles of the added cyclododecatriene, $CDT_1$ is the number of moles of the cyclododecatriene after reaction, and $CDDN_1$ is the number of moles of the cyclododecadiene. In this case, the cyclododecadiene (CDDN) is a product obtained in unfinished hydrogenation in which only one double bond of three double bonds of cyclododecatriene is hydrogenated and two double bonds remain.

In addition, the recovered selective homogeneous hydrogenation catalyst may satisfy the following Relational Expression 2.

$$90 \leq S_2/S_1 \times 100 \leq 100 \quad \text{[Relational Expression 2]}$$

In Relational Expression 2, $S_1$ is a selectivity (%) in the initial selective hydrogenation performed before the recovering of the selective homogeneous hydrogenation catalyst, and $S_2$ is a selectivity (%) in the selective hydrogenation performed using the recovered selective homogeneous hydrogenation catalyst as a catalyst.

More preferably, the recovered selective homogeneous hydrogenation catalyst may satisfy $95 \leq S_2/S_1 \times 100 \leq 100$. Still more preferably, the recovered selective homogeneous hydrogenation catalyst may satisfy $98 \leq S_2/S_1 \times 100 \leq 100$.

In this case, the selectivity may be calculated after the selective hydrogenation is performed in a state where reaction conditions such as a content of each of components, a reaction temperature, pressure, and time, and the like are adjusted to be the same as each other. The selectivity may be calculated by the following Calculation Formula 2.

$$\text{Selectivity(\%)} = CDEN_1/(CDEN_1 + CDAN_1) \times 100 \quad \text{[Calculation Formula 2]}$$

In Calculation Formula 2, $CDEN_1$ is the number of moles of the produced cyclododecene, and $CDAN_1$ is the number of moles of cyclododecane that is a produced by-product.

In addition, the present invention provides a method for reusing a recovered selective homogeneous hydrogenation catalyst includes: a step of synthesizing cyclododecene by selectively hydrogenating a first reaction solution containing cyclododecatriene, triphenylphosphine, formaldehyde, and ruthenium chloride, the cyclododecene being synthesized by preparation of a selective homogeneous hydrogenation catalyst from the triphenylphosphine, the formaldehyde, and the ruthenium chloride during the selective hydrogenation; a step of distilling and separating unreacted cyclododecatriene and cyclododecadiene, and the cyclododecene that is a product from a second reaction solution in which the cyclododecene synthesis is completed, and recovering the selective homogeneous hydrogenation catalyst; and a step of synthesizing cyclododecene by re-adding the recovered selective homogeneous hydrogenation catalyst to a third reaction solution containing cyclododecatriene and secondarily selectively hydrogenating the recovered selective homogeneous hydrogenation catalyst.

In this case, the step of synthesizing the cyclododecene by selectively hydrogenating the first reaction solution containing cyclododecatriene, triphenylphosphine, formaldehyde, and ruthenium chloride, the cyclododecene being synthesized by the preparation of the selective homogeneous hydrogenation catalyst from the triphenylphosphine, the formaldehyde, and the ruthenium chloride during the selective hydrogenation; and the step of distilling and separating the unreacted cyclododecatriene and cyclododecadiene, and the cyclododecene that is the product from the second reaction solution in which the cyclododecene synthesis is completed, and recovering the selective homogeneous hydrogenation catalyst are the same as those in the method for recovering a selective homogeneous hydrogenation catalyst described above. Therefore, an overlapped description thereof will be omitted.

Thereafter, after the distillation and separation and the recovering of the selective homogeneous hydrogenation catalyst are completed, the step of synthesizing the cyclododecene by re-adding the recovered selective homogeneous hydrogenation catalyst to the third reaction solution containing the cyclododecatriene and secondarily selectively hydrogenating the recovered selective homogeneous hydrogenation catalyst may be performed.

In this case, the second selective hydrogenation for synthesizing the cyclododecatriene may be performed by an existing known method.

As a specific example, a solvent containing ethanol may be further added to the third reaction solution, in addition to the cyclododecatriene. Since the ethanol has a high dielectric constant, the reaction between the reactants may be further activated in the selective hydrogenation, such that the conversion ratio and the selectivity may be improved. A use amount of the ethanol is not particularly limited as long as selective hydrogenation to cyclododecatriene may be performed. Preferably, the amount of ethanol to be added may be 1 to 20 parts by weight, more preferably 2 to 15 parts by weight, and still more preferably 3 to 10 parts by weight, with respect to 100 parts by weight of the cyclododecatriene. However, this is only a preferred example, and the present invention is not limited thereto.

In an embodiment of the present invention, the second selective hydrogenation may be performed at a temperature of 120 to 200° C. and a pressure of 10 to 80 bar, more preferably at a temperature of 140 to 180° C. and a pressure of 20 to 60 bar, and still more preferably at a temperature of 150 to 175° C. and a pressure of 20 to 40 bar. However, this is only a preferred example to improve the conversion ratio and the selectivity, and the present invention is not limited thereto.

Hereinafter, methods for recovering and reusing a selective homogeneous hydrogenation catalyst according to the present invention will be described in detail with reference to Examples. However, each of the following Examples is only one reference example for describing the present invention in detail, and the present invention is not limited thereto and may be implemented in various forms.

Unless otherwise defined, all technical terms and scientific terms used herein have the same meanings as commonly understood by those skilled in the art to which the present invention pertains. The terms used herein are only for effectively describing a certain example rather than limiting the present invention. In addition, unless otherwise stated in the specification, the unit of added materials may be wt %.

Example 1

Cyclododecatriene (CDT), ruthenium chloride ($RuCl_3$), triphenylphosphine (TPP), and formaldehyde were added in a molar ratio of 7,500:1:110:220, a reaction solution was stirred under a condition of 6 bar of hydrogen, and selective hydrogenation was performed under a condition of 160° C. and 20 bar were maintained for 2 hours. In this case, the reaction was performed in a stirred-tank reactor provided with a gas induction hollow stirrer.

The selective hydrogenation was performed for 2 hours, the temperature was cooled to 30° C. or lower under a nitrogen condition to recover the reaction solution, and the reaction solution was distilled in a distillation apparatus at 0.1 bar or less and 110° C.

After the distillation was completed, the temperature was cooled to 30° C. or lower under a nitrogen condition to recover a selective homogeneous hydrogenation catalyst.

Example 2

Selective hydrogenation was performed by re-adding the recovered selective homogeneous hydrogenation catalyst to the reaction solution in the same manner as that of Example 1.

More specifically, cyclododecatriene (CDT) and the recovered selective homogeneous hydrogenation catalyst were added in a molar ratio of 7,500:1, the reaction solution was stirred under a condition of 6 bar of hydrogen, and selective hydrogenation was performed under a condition of 160° C. and 20 bar were maintained for 2 hours. In this case, the reaction was performed in a stirred-tank reactor provided with a gas induction hollow stirrer.

The selective hydrogenation was performed for 2 hours, the temperature was cooled to 30° C. or lower under a nitrogen condition to recover the reaction solution, and the reaction solution was distilled in a distillation apparatus at 0.1 bar or less and 110° C.

After the distillation was completed, the temperature was cooled to 30° C. or lower under a nitrogen condition to recover a selective homogeneous hydrogenation catalyst.

Experimental Example 1

<Evaluation of Conversion Ratio and Selectivity>

The conversion ratio and the selectivity of the recovered selective homogeneous hydrogenation catalyst of each of Examples 1 and 2 were calculated. The results are shown in Table 1.

TABLE 1

|  | Conversion ratio (%) | Selectivity (%) |
| --- | --- | --- |
| Example 1 | 98.7 | 98.5 |
| Example 2 | 98.7 | 97.1 |

As a result, as shown in Table 1, it could be confirmed that the conversion ratio and the selectivity in the initial selective hydrogenation were almost the same as those in the second selective hydrogenation performed using the recovered selective homogeneous hydrogenation catalyst. Specifically, it could be confirmed that $C_2/C_1 \times 100$ was 100, which showed that the conversion ratios in two reactions were the same as each other, and $S_2/S_1 \times 100$ was 98.6, which showed that the selectivities in two reactions were almost the same as each other.

Hereinabove, although the present invention has been described by specific matters and limited embodiments, they have been provided only for assisting in the entire understanding of the present invention. Therefore, the present invention is not limited to the above embodiments. Various modifications and changes may be made by those skilled in the art to which the present invention pertains from this description.

Therefore, the spirit of the present invention should not be limited to these embodiments, but the claims and all modifications equal or equivalent to the claims are intended to fall within the scope and spirit of the present invention.

The invention claimed is:
1. A method for recovering a selective homogeneous hydrogenation catalyst, comprising:
   a step of synthesizing cyclododecene by selectively hydrogenating a reaction solution containing cyclododecatriene, triphenylphosphine, formaldehyde, and ruthenium chloride, wherein a selective homogeneous hydrogenation catalyst is prepared from the triphenylphosphine, the formaldehyde, and the ruthenium chloride during the selective hydrogenation;
   a step of distilling and separating unreacted cyclododecatriene and cyclododecadiene, and the cyclododecene that is a product from the reaction solution in which the cyclododecene synthesis is completed; and a step of recovering the selective homogeneous hydrogenation catalyst at a temperature of 10 to 30° C. and at a pressure of 0.1 bar or less or in a nitrogen atmosphere, wherein a molar ratio of the ruthenium chloride:the triphenylphosphine:the formaldehyde is 1:100 to 300:150 to 500, and wherein the selective hydrogenation is performed in a stirred-tank reactor provided with a gas induction hollow stirrer.

2. The method of claim 1, wherein the distillation and separation is performed at a temperature of 100 to 200° C. and a pressure of 0.5 bar or less.

3. The method of claim 1, wherein the recovered selective homogeneous hydrogenation catalyst satisfies the following Relational Expression 1, $$90 \leq C_2/C_1 \times 100 \leq 100 \qquad \text{[Relational Expression 1]}$$

in Relational Expression 1, $C_1$ is a conversion ratio (%) in the initial selective hydrogenation performed before the recovering of the selective homogeneous hydrogenation catalyst, and $C_2$ is a conversion ratio (%) in the selective hydrogenation performed using the recovered selective homogeneous hydrogenation catalyst as a catalyst.

4. The method of claim 1, wherein the recovered selective homogeneous hydrogenation catalyst satisfies the following Relational Expression 2, $$90 \leq S_2/S_1 \times 100 \leq 100 \qquad \text{[Relational Expression 2]}$$

in Relational Expression 2, $S_1$ is a selectivity (%) in the initial selective hydrogenation performed before the recovering of the selective homogeneous hydrogenation catalyst, and $S_2$ is a selectivity (%) in the selective hydrogenation performed using the recovered selective homogeneous hydrogenation catalyst as a catalyst.

5. The method of claim 1, wherein hydrogen gas present in a gas phase at an upper portion of the stirred-tank reactor is supplied to the reaction solution through a hollow portion of the gas induction hollow stirrer.

6. The method of claim 1, wherein the first reaction solution further contains a catalyst activator containing acetic acid.

7. The method of claim 6, wherein the catalyst activator is added in an amount of 0.01 to 2 parts by weight with respect to 100 parts by mass of the cyclododecatriene.

8. The method of claim 1, wherein the selective hydrogenation is performed at a temperature of 120 to 200° C. and a pressure of 10 to 80 bar.

9. A method for reusing a recovered selective homogeneous hydrogenation catalyst, comprising:

a step of synthesizing cyclododecene by selectively hydrogenating a reaction solution containing cyclododecatriene, triphenylphosphine, formaldehyde, and ruthenium chloride, wherein a selective homogeneous hydrogenation catalyst is prepared from the triphenylphosphine, the formaldehyde, and the ruthenium chloride during the selective hydrogenation;

a step of distilling and separating unreacted cyclododecatriene and cyclododecadiene, and the cyclododecene that is a product from the reaction solution in which the cyclododecene synthesis is completed;

a step of recovering the selective homogeneous hydrogenation catalyst at a temperature of 10 to 30° C. and at a pressure of 0.1 bar or less in a nitrogen atmosphere; and a step of synthesizing cyclododecene by re-adding the recovered selective homogeneous hydrogenation catalyst to a reaction solution containing cyclododecatriene and secondarily selectively hydrogenating the reaction solution in which the recovered selective homogeneous hydrogenation catalyst was re-added, wherein a molar ratio of the ruthenium chloride:the triphenylphosphine:the formaldehyde is 1:100 to 300:150 to 500, and wherein the selective hydrogenations are performed in a stirred-tank reactor provided with a gas induction hollow stirrer.

\* \* \* \* \*